(12) United States Patent
Folestad et al.

(10) Patent No.: US 7,825,668 B2
(45) Date of Patent: Nov. 2, 2010

(54) SPECTROSCOPIC METHOD

(75) Inventors: Staffan Folestad, Mölndal (SE); Lubomir Gradinarsky, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 548 days.

(21) Appl. No.: 11/793,391

(22) PCT Filed: Dec. 20, 2005

(86) PCT No.: PCT/SE2005/001973

§ 371 (c)(1),
(2), (4) Date: Jun. 19, 2007

(87) PCT Pub. No.: WO2006/068597

PCT Pub. Date: Jun. 29, 2006

(65) Prior Publication Data

US 2008/0116056 A1    May 22, 2008

(30) Foreign Application Priority Data

Dec. 22, 2004   (SE)   ................................. 0403152

(51) Int. Cl.
*G01R 27/04* (2006.01)
(52) U.S. Cl. ....................... 324/637; 324/639; 324/642
(58) Field of Classification Search .................. 324/637
See application file for complete search history.

(56) References Cited

U.S. PATENT DOCUMENTS

| 4,211,970 | A |  | 7/1980 | Fitzky et al. |
| 4,485,284 | A |  | 11/1984 | Pakulis |
| 5,046,356 | A |  | 9/1991 | Osaki et al. |
| 7,068,050 | B2 | * | 6/2006 | Steele et al. ................. 324/640 |
| 7,483,130 | B2 | * | 1/2009 | Baumberg et al. ........... 356/301 |
| 2003/0100938 | A1 | * | 5/2003 | Rubenchik et al. ........... 623/1.1 |
| 2003/0115938 | A1 |  | 6/2003 | Wu |
| 2007/0211834 | A1 | * | 9/2007 | Johnson ...................... 375/343 |

FOREIGN PATENT DOCUMENTS

| EP | 0 971 227 | 1/2000 |
| GB | 2 277 803 | 11/1994 |
| GB | 2 359 630 | 8/2001 |
| JP | 62-127656 | 6/1987 |
| JP | 2-52244 | 2/1990 |
| JP | 08 178871 | 7/1996 |
| JP | 2004-144513 | 5/2004 |

\* cited by examiner

*Primary Examiner*—Thomas Valone
(74) *Attorney, Agent, or Firm*—Finnegan, Henderson, Farabow, Garrett & Dunner, LLP

(57) ABSTRACT

A method related to a process for treating pharmaceutical contents in a pharmaceutical processing vessel is provided. The contents have a number of predefined parameters of variable values. According to the method electromagnetic radiation of various frequencies is transmitted into the vessel and its contents. Electromagnetic radiation which has interacted with the contents is received. Based on the received electromagnetic radiation, a respective value of a physical quantity related to the contents is determining for a plurality of said frequencies. A combination of values of said predefined parameters which would, for said plurality of frequencies, approximately result in the determined values of said physical quantity is determined.

20 Claims, 4 Drawing Sheets

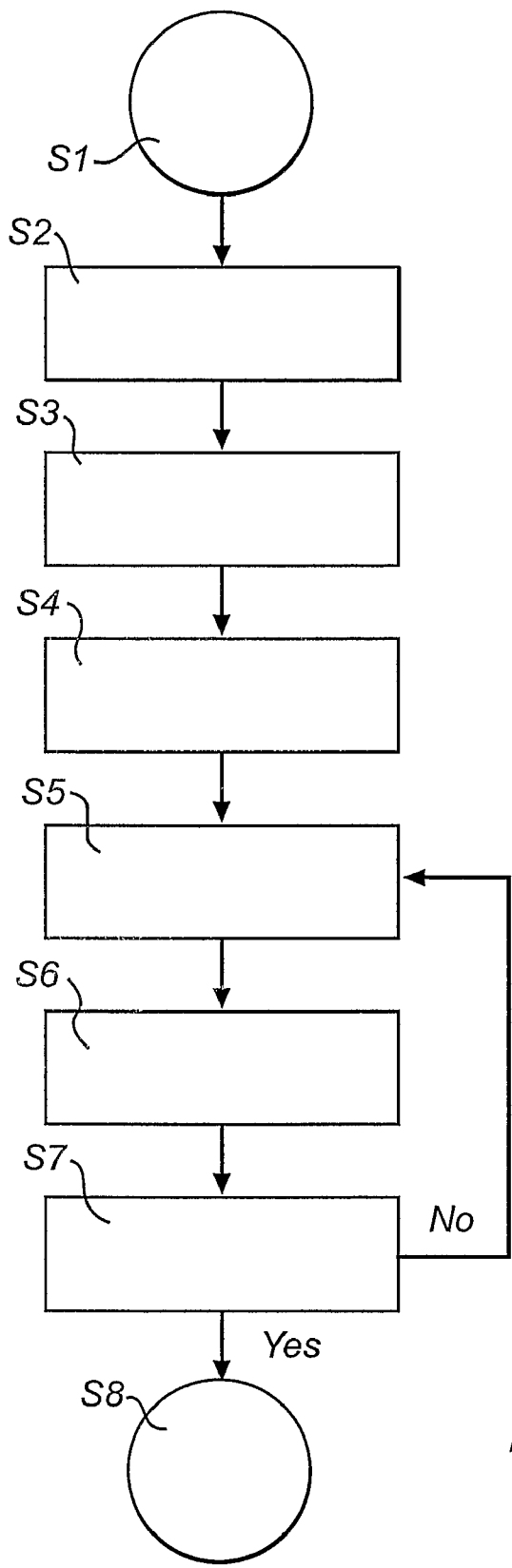
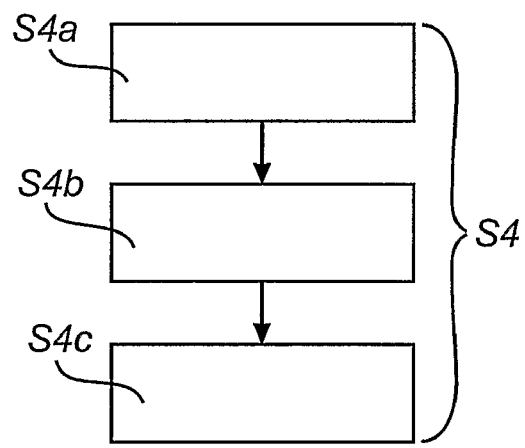
Fig. 2b
Fig. 2a

SPECTROSCOPIC METHOD

TECHNICAL FIELD

The present invention concerns a method related to a process for treating pharmaceutical contents in a pharmaceutical processing vessel. In said method the interaction of electromagnetic radiation with said contents is used for spectral analysis.

BACKGROUND OF THE INVENTION

The production of pharmaceutical solid dosage forms involves a multistage operation. It requires between six and eight unit processes, such as charging of raw materials, milling, granulation, drying, blending, compression, coating and packaging. In some of these processes the treated material contents may change their properties. For instance, in a granulation process, solid materials may be mixed with a liquid, wherein the liquid bounding state, the liquid contents, the temperature and density of the mixture is changing as the process progresses. In a drying process the liquid content is reduced, and the density and the temperature may change during the process. A coating process may be performed either in a fluidised bed wherein particles, so-called nuclei, are sprayed with a specific coating liquid, or by passing the particles through a spray dust of said liquid, or by other generally used coating techniques, such as melting, aggregation etc., wherein the material properties may change as the coating process progresses.

The quality of the different processes depends on different physical and/or chemical properties of the materials used in the process, such as chemical composition, local inhomogeneities, physical and chemical homogeneity, density, mechanical properties, static parameters, modulus, tensile strength, elongation at break, compression, ductility, viscoelastic parameters, morphology, macro- and microscopic properties, amorphous and/or crystallinity, permeability, porosity, aggregation, wettability, degree of coalescence/maturity, stability and ability to resist chemical and/or physical degradation.

There are also other properties not listed above. In order to keep the quality of the material at the end of a unit process, it is desirable to control that process.

In an industrial plant for manufacturing pharmaceutical products, selected process parameters are monitored and controlled to achieve a desired quality of the finished product. Such process parameters could include, for example, the motor output in the granulation vessel, the flow rate of water into the granulation vessel, the pressure in the coating vessel, the temperature in the drying vessel, the flow rate and temperature of gas and coating liquid supplied to the coating vessel, etc. However, the influence of such global process parameters on the processes, and ultimately on the properties of the end product, is known only from experience in a specific plant. Thus, a processing scheme is developed for each specific plant by extensive testing. When, for example, the size or shape of the vessels are changed during scaling up of the process the local environment of the materials in the vessels may be altered. This calls for time-consuming measurements and adjustments in order to regain the same properties of the end product.

There is also a need to improve existing manufacturing processes as well as to improve existing plants. Today, this is a laborious task since the influence of any change in the process scheme or the plant design on the end product has to be investigated by extensive testing, often in full scale. The same applies to the development of new products, for example when new types of material (solid or liquid) should be used.

For instance, in a high-shear granulation process it is common to monitor the process by measuring the power consumption of the motor which drives an agitator, impeller or propeller or some other mixing means inside the high-shear granulation vessel. That kind of monitoring is an indirect measurement which only provides information about the general state of the process. For developing process control parameters, the personnel may study many granulation processes, wherein different amounts of liquid has been added and with different power consumptions, and then choose one which provided a satisfactory granulation product. The parameters used for obtaining the satisfactory granulation, will consequently be used for future granulations. In other words, this known procedure is empirical and only provides an indirect control of the process. Thus, one limitation of the prior art methods in pharmaceutical process lies in their calibration. Apart from this laborious way to calibrate a process, in particular a granulation process, and the rather imprecise monitoring of measuring the power consumption for determining whether the granulation has reached a desired state, there is also a scaling-up problem. Scaling-up is not straight forward and therefore needs to be empirically adjusted. The power consumption pattern may be quite different in a full-scale high-shear granulation vessel in an manufacturing plant compared to a small vessel used in a laboratory. Scale-up issues are discussed in e.g. in A. Faure, P. York, R. C. Rowe, Process control and scale-up of pharmaceutical wet granulation processes: a review, European Journal of Pharmaceutics and Biopharmaceutics 52 (2001) 269-277.

An example of power consumption measurement may be obtained from an article by Gabriele Betz, Pascale Junker Bürgin and Hans Leuenberger, Power consumption measurement and temperature recording during granulation, International Journal of Pharmaceutics, Volume 272, Issues 1-2, 2004, pp. 137-149. The article and the references therein explain and demonstrate the application of power consumption measurements for indirect end-point determination of the high-shear granulation process. It also describes how additional measurements of the temperature may complement the process understanding. Another article on this subject is written by M. Bardin, P. C. Knight, J. P. K. Seville: On control of particle size distribution in granulation using high-shear mixers, Powder Technology 140 (2004), 169-175. It describes the indirect link of the particle size distribution during granulation to the power consumption, and also demonstrates the shortcomings of the method for coarse powders where no relation was directly identified.

In summary, even though there are methods of monitoring pharmaceutical processes, such as a high-shear granulation process, there still remains improvements to be made for alleviating the drawbacks of the above methods.

SUMMARY OF THE INVENTION

An object of the present invention is to improve the monitoring and/or control of a pharmaceutical process, in particular, but not limited to, a high-shear granulation process.

Another object is to provide a method which enables the monitoring of physical material parameter changes during the progress of a pharmaceutical process, in particular, but not limited to, a high-shear granulation process, and the controlling of the process on the basis of such monitoring.

These and other objects, which will become apparent in the following, are accomplished by the method defined in the accompanied independent claims.

The present invention is based on the insight that during processing of pharmaceutical materials or substances, a number of physical and/or chemical parameters are changed in the course of processing the materials. The invention is also based on the insight that by determining the combined effect of the parameters on a physical quantity related to the materials, information is obtainable and may be used for controlling the process. One such physical quantity is the dielectric constant or permittivity of the materials. The different parameters may contribute to the resulting value of the physical quantity to different extent and the resulting quantity value may depend on an electric field applied over the materials. The inventors of the present invention have realized that by applying, to the contents of a processing vessel, an electric field of various frequencies the quantity value versus the frequencies is obtainable. By matching a combination of parameters that would result in approximately said quantity value to frequency variation with the actually determined quantity values, useful information is obtainable about the process. The information may then be used for controlling the process.

According to a first aspect of the invention a method is provided, the method being related to a process for treating pharmaceutical contents in a pharmaceutical processing vessel, wherein the contents have a number of predefined parameters of variable values. The method comprises:

transmitting into the vessel and its contents electromagnetic radiation of various frequencies, receiving electromagnetic radiation which has interacted with the contents, determining for a plurality of said frequencies a respective value of a physical quantity related to the contents based on the received electromagnetic radiation, and determining a combination of values of said predefined parameters which would, for said plurality of frequencies, approximately or substantially result in the determined values of said physical quantity.

The inventive method may be implemented in processes in the manufacturing of different types of pharmaceutical products, such as pharmaceutical dosage forms, e.g. tablets or capsules.

It should be noted that the method is not limited to receiving the electromagnetic radiation of each transmitted frequency or to determine a physical quantity value for each transmitted frequency. However, the more frequencies that are detected and become associated with a value of a physical quantity related to the contents, the higher accuracy is obtainable when matching a combination of the predefined parameters to the obtained spectroscopic data. Also, a broad frequency range may provide a higher matching accuracy.

It should be noted that the determined combination of values of the parameters may be an estimate which does not necessarily correspond exactly to the real values of the contents, i.e. those values of the parameters which have actually resulted in the obtained spectroscopic data (physical quantity versus frequency). However, by using e.g. least square error methods or other suitable methods a satisfactory estimate is obtainable.

The contents may comprise any suitable pharmaceutical material or substance, and the terms "pharmaceutical material" and "pharmaceutical substance" are herein to be interpreted as including at least any one of the items from the group consisting of powders, powders in combination with a water or other liquid, solids, solids in combination with water or other liquid, slurries, liquids and suspensions. It may also be a combination of said items. It should also be understood that pharmaceutical materials and substances are not limited to meaning only one or more active components, but it may also mean one or more non-active components, generally referred to as excipients, or a combination of active and non-active components. It should also be understood that the general term "pharmaceutical contents" in the processing vessel is to be interpreted as not only comprising a "pharmaceutical material" or "pharmaceutical substance" according to the above, but also a gas such as air, and/or a liquid such as water, in particular gas and/or liquid trapped between pharmaceutical material particles, and also gas contained in the pharmaceutical material.

As mentioned above, said physical quantity may suitably be the dielectric constant of the material contents provided in the vessel. The advantage of monitoring the dielectric constant of the contents is that it may vary substantially as a function of the frequency of the interacting electromagnetic radiation. Since the dielectric constant $\in$ has a real part $\in'$ (permittivity) and an imaginary part $\in''$ (dielectric loss factor), wherein $\in = \in' - j\in''$, an alternative would be to only monitor the real or the imaginary part of the dielectric constant. Thus, according to at least one embodiment of the invention the method comprises determining for a plurality of said frequencies the respective dielectric constant of the contents based on the received electromagnetic radiation, and determining a combination of values of said predefined parameters which would, for said plurality of frequencies, approximately result in the determined dielectric constants. As an alternative to determining the total dielectric constant, it would be conceivable to determine only the real part or only the imaginary part thereof. The dielectric properties of the material is obtainable by measuring e.g. the attenuated, the reflected and/or the scattered signal amplitude and phase at the selected frequencies of operation.

By comparing the received with the transmitted electromagnetic radiation (wave) a phase change and/or amplitude change of the electromagnetic radiation (wave) information relating to the contents in the vessel is obtainable. The phase change and the amplitude change is dependent on the electromagnetic radiation interacting with the contents. The interaction may also have a frequency dependence (dispersive nature). The dielectric constant of the contents may be determined from the measured values of the phase and amplitude of the received electromagnetic radiation using the general electromagnetic theory for wave propagation. For any suitable measurement set-up a theoretical calculation could be performed relating the measured amplitude and phase changes to the dielectric constant of the contents in the vessel. There are different commercially available sensor devices which employ such calculations and provide an output of the value of the dielectric constant. Even though the dielectric constant, which takes into account both a change of phase and amplitude, may provide more distinguishable spectroscopic data, it would also be conceivable to observe only the phase change or only the amplitude change as a function of the frequencies of the transmitted electromagnetic radiation which has interacted with the contents in the pharmaceutical processing vessel. Therefore, according to at least one embodiment of the invention the method comprises comparing for a plurality of said frequencies the respective phase and/or amplitude change between the received and transmitted electromagnetic radiation, and determining a combination of values of said predefined parameters which would, for said plurality of frequencies, approximately result in the determined phase and/or amplitude changes.

As already mentioned the properties of the materials in the processing vessel affect the physical quantity to be measured. This effect could also have a dispersive nature. The contents may comprise different predefined parameters of variable values. One such parameter may be the temperature of the contents. Another one may be the density of the contents. A further parameter may be the water content. Because of the hydrogen atoms, the water molecules tend to form hydrogen bonds on the surface of other material molecules. Even though hydrogen bonds are rather week compared to chemical bonds, they restrict the free movement of the molecules. Hydrogen bonds therefore affect the dielectric constant of the water. Thus, other parameters may be the water state/bounding, or the fraction of water which is behaving as bulk/free water or as bound to other materials. When water becomes bound to other materials the molecules in the water will be tied with more bonds than in bulk water, thereby having less flexibility, which in turn will affect its dielectric properties. A measure of the strength of binding is the energy released per mole when the bonds are formed, the activation energy Q (kJ/mol). Another parameter may be the volumetric ratio of one or more substances in the contents, such substances suitably being pharmaceutical material, water and/or air.

Thus, as an elucidating example, the inventive method may be regarded as providing a spectroscopic plot wherein a value of a physical quantity, such as the above mentioned amplitude, phase or dielectric constant, is plotted against a range of frequencies. A respective value of each predefined parameter of the contents is determined so that the combination of these parameters of a material would approximately result in said plot if subjected to the same frequencies of electromagnetic radiation.

The combination of values of said predefined parameters may be determined in different ways. For instance, it may be determined by means of a theoretical physical modelling of the interaction of the radiation energy with the contents inside the vessel. In such case, a suitable model may be used which describes the physical quantity (e.g. dielectric constant of the contents, or amplitude and/or phase change) as a function of the predefined parameters (e.g. operating frequency, temperature, etc.). The model generally includes an equation having a number of unknown variables (e.g. temperature, liquid contents, volumetric ratios, etc.). Since a plurality of operating frequencies are known, and a value of the physical quantity has been determined for each frequency, an equation system may be provided in order to determine the unknown variables. The calculations or spectral analysis may suitably be performed automatically by an analysing unit, e.g. including a microprocessor or computer having an analysing program such as MATLAB®.

A theoretical model which has been found advantageous for determining the combination of values of said predefined parameters comprises solving the following equation for each dielectric constant $\varepsilon(f,T,LC)$ determined for a respective frequency:

$$\varepsilon^a(f, T, LC) = \varepsilon_L^a(f, T) \cdot V_L + \varepsilon_{Air}^a V_{Air} + \sum_{i=1}^{N} \varepsilon_{M_i}^a(f, T, LC) \cdot V_{M_i}$$

wherein, for a number of N different pharmaceutical materials, $V_{M_i}$ is the volumetric ratio of the i:th pharmaceutical material to the total contents volume V; $\varepsilon_{M_i}$ is the dielectric constant of the i:th pharmaceutical material; $V_L$ is the volumetric ratio of a liquid, such as water, to the total contents volume V; $\varepsilon_L$ is the dielectric constant of a liquid, such as water; $V_{Air}$ is the volumetric ratio of air to the total contents volume V; $\varepsilon_{Air}$ is the dielectric constant of air, which can generally be approximated to 1-j0; f is the frequency; T is the temperature of the contents in the vessel; LC is the liquid content of the material; and a is a power constant. The above equation may be solved for the real and/or the imaginary part of the dielectric constant.

Another way to determine the combination of values of said predefined parameters is by means of multivariate analytical methods such as Principal Component Analysis (PCA) or Projections to Latent Structures (PLS). In such an analysis a program is trained to perform estimations based on earlier measurements. This may be done by executing a process in a vessel and at different points of time a sample of the contents inside the vessel is taken for analysis. For each sample a number of parameters (e.g. temperature, water content, particle size distribution, etc.) may be determined by means of known analysing methods. Also for each point of time spectroscopic data is acquired in order to determine how the physical quantity (e.g. the dielectric constant) varies with the frequency. By varying the different parameters and making a multitude of measurements a large amount of data is acquired for different situations. A matrix of spectral data (A) may then be expressed as the product of a coefficients matrix (B) and a parameter matrix (C), i.e. A=BC. Since the parameters have been determined from the different samples, and since the spectral data has been measured, the coefficients in the coefficient matrix may be determined. Thus, in a subsequent process when measurements are performed in-line, the determined coefficient matrix may be used to predict approximate values of the then unknown parameters, without taking any samples.

Yet another way to determine the combination of values of said predefined parameters is by means of an empirical broad parameter space calibration. For instance, measurements may be performed in a laboratory environment and based on those measurements a suitable equation may be determined which is subsequently implemented in the industrial application.

It should also be understood that the step of determining the combination of values of said predefined parameters may be accomplished by means of any combination of the above described three different exemplifying ways.

Measurements using electromagnetic radiation in the microwave/THz region (microwave region is about 0.3-300 GHz and THz region is about 0.3-10 THz) will in general strongly depend on e.g. material density, temperature, water content (state), and the used frequency. For such cases, any one of the above described ways to determine said combination of values may allow for simultaneous retrieval of parameters from a broad spectrum measurement, and consequently they will all benefit from using a broadband spectroscopic measurement. Such broadband (e.g. a few GHz) spectral measurements of the responses (e.g. the dielectric constant) will enable simultaneous parameter estimation in dynamically changing processes.

It has been found particularly advantageous to obtain the spectroscopic data for electromagnetic radiation in the range of 100 MHz to 10 THz. Suitably the electromagnetic radiation has microwave frequencies as defined above. An advantage of using these frequencies, and in particular microwave frequencies is that microwave radiation penetrates the pharmaceutical materials better than other types of radiation, e.g. NIR (near infrared). Even though microwaves penetrate pharmaceutical materials, they are affected and become distorted, e.g. changed amplitude or phase, and the distortion may be different for different frequencies in said ranges, thereby providing usable spectroscopic data. Since microwaves have a relatively large penetration depth a larger sampling region is possible compared to the relatively limited surface measurements that would be possible with NIR. A larger sampling region means that adequate measurements may e.g. be performed in a large vessel in an industrial plant. When perturbing with a sample of materials, the absorption of the radiation depends on the concentration of the material components. However, in the NIR region it is not absorption that is dominating, but instead scattering which will disturb the measurement. In the microwave region there is strong absorption of water and scattering is lower compared to absorption, at least in the lower part of the microwave spectrum. Dry material, such as dry powder, is transparent to microwaves. Microwaves will almost only have information regarding water absorption or other liquids with high dielectric constant, thereby providing high selectivity. This makes microwaves useful for determining the value of for instance a parameter such as the state of the water (free or bound water) for the material contents. An advantage of using frequencies in the THz region is the additional information obtainable about the physical state of the material, due to other mechanisms or interactions beginning to act in said frequency region as e.g. intermolecular interactions.

The method according to the present invention has been found advantageous in connection with a high-shear granulation process for processing the contents in a high-shear granulation vessel. In such a process an active ingredient is generally mixed with a filler ingredient in a homogenous way. If the ingredients, such as powders, would only be dry-mixed, then there would be a potential risk of small particles being separated from larger particles during powder transportation. Therefore, the ingredients, such as powders, are mixed with some water or other liquid acting as a binder. The evolution of this process is the sum of several sub-processes, e.g. one sub-process in which the particles are building-up (coalescence) and one sub-process in which they are disintegrating (breakage), whereby the mixture will obtain a predetermined size distribution. While the conventional monitoring of the power consumption of a motor is a rather blunt instrument, the present invention allows continuous monitoring of the state of the contents in the vessel, thereby enabling more accurate information concerning the progress of the process to be obtained. For instance, in high-shear granulation the water binding state is a relevant parameter for determining how far the process has progressed. However, it should be noted, that the method according to the present invention is not only applicable to high-shear granulation processes, but also to other types of granulations processes, such as spray granulation. Furthermore, the method according to the present invention may also be applicable to other pharmaceutical processes, such as those described herein under the heading "Background of the invention".

The method according to the present invention may also be implemented in a process for drying the contents in a drying vessel. For instance, one predefined parameter of the contents may be the volumetric ratio of air to the total contents volume, another parameter may be the volumetric ratio of a liquid, and yet another parameter may be the volumetric ratio of a pharmaceutical material. By determining the values of these parameters information is obtainable concerning the progress of the drying process. For instance, in the beginning of the drying process there may be some free water present which will gradually disappear whereby its volumetric ratio will become zero. As the drying continuous some bound water will also evaporate and once a certain wetness of the pharmaceutical material has been reached, the drying process may be stopped whereby excessive drying time may be avoided.

The method according to the present invention may also be implemented in a process for blending the contents in a blending or mixing apparatus. Similarly to granulation and drying processes the pre-defined parameters may be different volumetric ratios and wetness. For instance, the estimate of the wetness may be used for controlling the required wetness of the contents so as to be suitable for a subsequent tabletting procedure.

The method according to the present invention may be implemented as a single measurement or multiple measurement method. In accordance with at least one embodiment of the invention the desired process information is obtainable by executing only once the transmission and reception of electromagnetic radiation, and the subsequent determination of the value. This may for instance be the case if the desired process information is related to the properties of the contents before they are processed, or alternatively some other single point of time during the actual process. By knowing the properties of the contents at a specific time (e.g. before the start of the process), the properties of the contents at the end of the process may be estimated if the processing is performed in a predefined manner. If these estimated end point properties are considered to be unsuitable, some process parameters may be controlled so as to obtain satisfactory end point properties. Even though a one-time measurement may provide enough information, it is also conceivable to perform measurements at several points of time during the process.

In accordance with at least one embodiment of the invention, the steps of transmitting electromagnetic radiation, receiving electromagnetic radiation and determining said values of a physical quantity are performed continuously or repeatedly for obtaining data related to the progress of the process. By continuously monitoring the progress of the process (or at least at several occasions) there are provided several opportunities for adequately controlling the process. The spectrometric measurement may be performed continuously during only a part of the pharmaceutical process, during several parts thereof or during the entire process. The continuous or repeated measurement generates a sequence of measurement values of said physical quantity and allows the combination of values of parameters to be determined for several points of time. It should be noted that in relation to the measurements described in this paragraph, the term "continuous" is to be interpreted to include measurements at several discrete occasions which are not performed at random or arbitrarily, but preferably rather with a certain repetition rate.

Even though the process may be controlled based on a one-time measurement, a more dynamical control is achievable in connection with continuous or repeated monitoring of the process. According to at least one embodiment of the invention the process is controlled on basis, at least partly, of at least one parameter value from the determined combination of values. It may be determined if said at least one parameter value deviates from a reference value. The information obtainable from this deviation may be related to a state of the process. The process may suitably be controlled based, at least partly, on said information. For instance, if it is determined that at a certain point of time the water content is lower than a reference value, more water may be added to the contents inside the pharmaceutical processing vessel.

Apart from the above example of controlling the amount of water (or other liquid), there are a number of other process parameters that may suitably be controllable. For instance, a process parameter may be the speed or rate, such as volume per time unit, of water (or other liquid) introduced into the processing vessel. Another controllable process parameter is the actual point of time for introducing water or other liquid into the processing vessel. Another process parameter is the point of time for ending the process. Yet another process parameter may be the place or location at the vessel for introducing water or other liquid, or even the direction of the nozzles from which it is introduced. The output or rotational speed of a mixing device, such as a propeller, agitator or impeller, and the angle of such a mixing device may be other controllable process parameters. Note that the controllable process parameters are not the same as the parameters of the contents (contents parameters) which are to be estimated. However, the process parameter are suitably controlled based on the estimate of the contents parameters.

From the above it should be clear that, in accordance at least one embodiment of the invention, measurements are used for defining the pharmaceutical process in order to control the process.

As mentioned previously, it may sometimes be desirable to perform the measurements according to the invention before starting the processing of the pharmaceutical material in the pharmaceutical processing vessel. This allows initial data to be obtained for prediction of a process path or process progress. For instance, even though the pharmaceutical material provided by a supplier is said to have a certain water content, it may have changed e.g. during transportation and be different at the time when it is inserted into the processing vessel. Thus, by determining the relevant combination of values of the predefined parameters a prediction may be made on how the process will progress if certain conditions are met, e.g. if certain process parameters are controlled in a known manner. Thus, according to at least one embodiment of the invention, the steps of transmitting electromagnetic radiation, receiving electromagnetic radiation, determining values of a physical quantity, and determining said combination of values of predefined parameters are performed before starting the processing of pharmaceutical materials. However, said embodiment may also include additionally performing said steps during the processing.

In some cases the step of determining said combination of values of predefined parameters may be performed after the processing of the pharmaceutical contents in the vessel is completed, in accordance with at least one embodiment of the invention. This may be advantageous for follow-up investigation or analysis. In other words the process development or progress may be archived by storing the obtained spectroscopic data related to the physical quantity as a function of the operating frequency, wherein the data need not be analysed immediately, but possibly at a later stage if desired. If for instance a product, such as a tablet, turns out to have some interesting or unexpected properties, the stored data may be retrieved to investigate what part of the process may have caused this. If the unexpected property of the product is undesired, and its cause is confirmed after having checked the estimated values of the parameters during the process (e.g. at several points of time if continuous measurements have been performed) future processing of pharmaceutical materials may be altered to avoid the flaw. On the other hand if the interesting or unexpected properties are of positive nature, then an analysis of the parameter evolution during the process may be used for enabling achievement of similar good results in the future.

According to at least one embodiment of the invention, as an alternative to performing the step of determining said combination of values of predefined parameters after the completion of the process, it would also be conceivable to determine said combination already during the process, while the information extractable from such a determination is evaluated only after the completion of the process.

A further alternative would be to perform at a later stage not only the step of determining said combination of values of predefined parameters, but also to perform the step of determining the values of the physical quantity as a function of frequency after the processing of the pharmaceutical material has been completed. Thus, the electromagnetic radiation may be received and the information it carries may be stored during the process without immediately determining the values of the relevant physical quantity.

The electromagnetic radiation may be transmitted into the vessel by means of any suitable transmitter system comprising an antenna or array of antennas. Likewise, the electromagnetic radiation that has interacted with the pharmaceutical contents inside the vessel may be received by means of any suitable receiver system comprising an antenna or array of antennas. It should be noted that a unit may function as both transmitter and receiver, wherein the unit transmits electromagnetic radiation and thereafter receives the interacted electromagnetic radiation. It should also be noted that several transmitter and receiver systems may be used in connection with one vessel, e.g. depending on the dimension and geometry of the vessel.

Another alternative is to provide an array of transmitters and/or receivers on a common module. Such transmitter/receiver arrays may be provided in one-dimensional format, wherein the transmitters and/or receivers are arranged along a line, or in a two-dimensional format, wherein the transmitters and/or receivers are arranged in a rectangular matrix. Other formats are also possible. This type of array provided as a module may either be regarded as a large antenna made up of several sub-antennas, or each transmitter and/or receiver on the module may be regarded as a plurality of stand-alone antennas. Said plurality of antennas may therefore be regarded as located at essentially the same location relative to the processing vessel or possibly as located at "different" locations but only separated by a relatively short distance. It should also be understood that several arrays may be used simultaneously for measurement on a processing structure. An advantage of using an array is that the width and direction of the transmitted electromagnetic radiation beam may be controlled by selectively activating a number of sub-antennas.

Transmitter and receiver systems may be implemented either as devices which may be introduced into the interior of the processing vessel or as non-invasive and non-destructive antennas for remote assessment. In the latter case, the processing vessel may be provided with a window which is transparent to the frequencies of the electromagnetic radiation to be transmitted. The non-invasive measurement is well-suited at least for the microwave/THz region.

By implementing several pairs of transmitters and receivers a two and/or three dimensional distribution of the predefined parameters may be estimated, e.g. by using tomographic methods. Thus, it is possible to detect e.g. different temperatures or wetness in different parts of the contents in the processing vessel, and thus the process may be controlled in response to the determined distribution. Another way to retrieve this type of spatial distribution would be to use a single pair or transmitter and receiver and to make several consecutive measurements of the moving contents with a high sampling rate. In this way the measured temporal variability may be related to the spatial information.

From the above it should be clear that the present invention provides new possibilities for monitoring and controlling pharmaceutical processes. The possibility to implement such a system in-line and at the same time to keep any process cleanness requirements are other additional benefits.

The present invention, using a plurality of frequencies, allows a set of parameters to be estimated substantially at the same time, wherein the parameters include both material specific parameters (such as the water content) and the physical state of the material (such as density and temperature).

It should also be clear that the present invention is not limited to batch processes in which a processing vessel receives a batch of material, processes the material, and receives a new batch when the previous batch has been removed from the vessel. On the contrary, the present invention is applicable to a continuous process as well as a batch process. Thus, the present invention is applicable in a continuous process wherein the contents flow without interruption through a vessel, such as a pipe, and during the flow becomes processed. Thus, the content parameters may be determined regardless of the contents being treated in a batch or in a continuous process.

BRIEF DESCRIPTION OF THE DRAWINGS

FIGS. 2a and 2b illustrate a flow chart for a procedure in which an embodiment of the method according to the present invention is implemented.

DETAILED DESCRIPTION OF THE DRAWINGS

Figure 1:
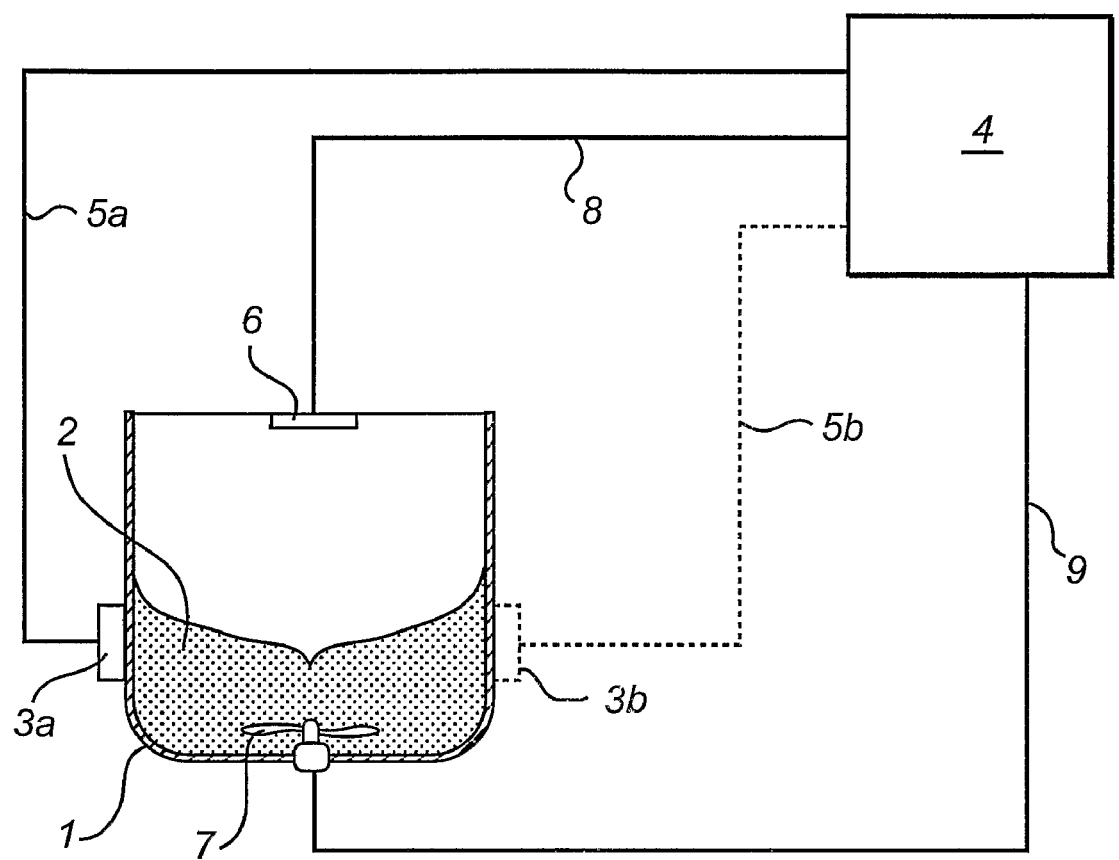
FIG. 1 illustrates schematically a processing vessel provided with a set-up for implementing the method according to the present invention.

FIG. 1 illustrates schematically a processing vessel 1 provided with a set-up for implementing the method according to the present invention. The processing vessel 1 in this figure is illustrated as a high-shear granulation vessel in which an active ingredient is mixed with a filler and a binding substance, such as water. However, the inventive method is also applicable to other types of processing vessels in which a pharmaceutical material 2 is processed.

The vessel wall is provided with a first probe 3a, such as an antenna or array of antennas. The first probe 3a may function as both a transmitter and receiver. Thus, it may transmit electromagnetic radiation and receive the reflected electromagnetic radiation that has interacted with the pharmaceutical contents 2 inside the vessel 1. Alternatively, as illustrated by the broken lines, a second probe 3b (antenna or array of antennas) may be provided, wherein one of the probes may be used for transmitting electromagnetic radiation and the other probe may be used for receiving electromagnetic radiation. Thus, the set-up may include either a reflection mode or transmission mode of operation. The probes 3a, 3b are suitably operated in the microwave or THz frequency region so as to achieve a satisfactory penetration depth of the electromagnetic radiation. The probes 3a, 3b may be insertable through the wall of the vessel 1 or be arranged to transmit and receive electromagnetic radiation outside the vessel 1 through a window which is at least partly transparent to electromagnetic radiation. If some other frequency region is used, such as NIR, it may be suitable to use insertable probes.

An analysing and control unit 4 is connected at least to one of the probes which receives the electromagnetic radiation. The analysing and control unit 4 is herein illustrated with wires 5a, 5b connected to the two probes 3a and 3b, respectively. However, the analysing and control unit 4 may also be operatively connected to said probes 3a, 3b by other means, e.g. radio control or coaxial lines wherein electromagnetic waves are conducted all the wave to the analysing and control unit 4.

The analysing and control unit 4 controls the transmission and reception of electromagnetic radiation, in particular the plurality of frequencies used for the radiation. However, it would also be conceivable to have a separate unit which controls the operating frequencies of the probes. Based on the received electromagnetic radiation, a respective value of a physical quantity, such as the dielectric constant of the contents inside the vessel 1, is determined by the analysing and control unit 4 for a plurality of the received frequencies. Alternative physical quantities may be only the real or only the imaginary part or the dielectric constant, or the phase or amplitude change. The resulting spectroscopic data may be stored for later analysis or may be immediately analysed. Thus, analysing and control unit 4 may determine a combination of values of predefined physical contents parameters, such as temperature, water content etc, which would, for said plurality of frequencies, approximately result in said spectroscopic data.

Based on the results of the determination of the estimated values of the parameters of the contents 2, the processing inside the vessel 1 may be controlled either manually or automatically. For instance, the system may suitably include a feed-back loop for automatically controlling the system, or alternatively an alert signal may be activated for an operator to take action manually. Suitably, if one or more of the estimated parameter values differ from stored reference values, the analysing and control unit 4 automatically initiates a process control. The vessel 1 is provided with a water supply arrangement 6, e.g. comprising a nozzle or system of nozzles, for adding water to the contents 2 of the vessel 1. The vessel 1 is also provided with a mixing arrangement 7, e.g. an impeller, for agitating and mixing the contents 2. The analysing and control unit 4 is operatively connected by wires 8 and 9, respectively, or by other means, to both the water supply arrangement 6 and the mixing arrangement 7. Thus, if for instance, a parameter such as water content is determined to be too low, the analysing and control unit 4 may control the water supply arrangement 6 so that water is added to the contents 2 of the vessel 1. Another example may be that the amount of water is satisfactory, but not enough surface water has formed on the material to sufficient extent (surface water is relevant for the process of coalescence to begin), in case of which the control and analysing unit 4 may control the operation of the mixing arrangement 7 so as to speed up the forming of such surface water.

Other types of process control and measurements may also be applied. For instance, the rate of addition of water into the vessel may be controlled. The change in amount of water in the vessel may be checked for conformity with the desired water addition rate. The homogeneity of the water distribution may be measured e.g. by checking if a number of consecutive sample measurements show substantially the same amount of water in each sample. Also, the three dimensional distribution of the wetness may be measured and controlled.

Further types of control and measurement are possible, some of which have been described under the heading "Summary of the invention".

FIGS. 2a and 2b illustrate a flow chart for a procedure in which an embodiment of the method according to the present invention is implemented. As shown in FIG. 2a the procedure is initiated by a general starting step S1, which may include any suitable preparations of a processing vessel. Next, in a step S2, the pharmaceutical materials are introduced into the processing vessel. The actual process for processing the pharmaceutical materials is started in a step S3, which in case of a granulation process may be dry-mixing of the pharmaceutical materials. Thereafter, in a step S4, an initial measurement and analysis is be performed in accordance with the inventive method.

As can be seen separately in FIG. 2b, the step S4 may be divided into three sub-steps. In a first sub-step S4a, a transmitter is controlled to transmit into the vessel and its contents, in this case the pharmaceutical materials, an electromagnetic radiation of various frequencies. In a following second sub-step S4b, a receiver is controlled to receive electromagnetic radiation which has interacted with the contents. In a subsequent sub-step S4c, an analysing and control unit is arranged to determine for a plurality of said frequencies, based on the received electromagnetic radiation, a respective value of a physical quantity (such as dielectric constant) related to the contents, and also to determine a combination of values of predefined parameters which would, for said plurality of frequencies, approximately result in the determined values of said physical quantity. As mentioned previously, an example of a predefined parameter may be the temperature, water state (level of hydrogen bounding) or water content etc.

Based on the result of the initial measurement and analysis in step S4, one or more process parameters are controlled in a step S5 (see FIG. 2a). Since pharmaceutical materials will not always have identical properties when delivered from a supplier of the materials, an initial measurement and analysis provides information on how to control the process at an early stage. For instance, in case of a granulation process, if it is determined in step S4 that the water content after the dry-mixing is lower than usual, there will be more addition of water into the vessel in step S5 compared to other occasions. A new measurement and analysis is made in a step S6, which corresponds to that previously made in step S4, including the sub-steps S4a, S4b and S4c. The result of the measurement and analysis is evaluated in a step S7, wherein it is checked whether the estimated values of the parameters are close enough to reference values, i.e. in case of a granulation process, whether the contents have been mixed satisfactorily and obtained the desired properties. If no, then the procedure is returned to step S5, wherein the relevant process parameter or parameters are controlled in order to attain the desired properties of the contents. After a subsequent measurement and analysis in step S6 it is again checked in step S7 whether or not defined conditions are met. When finally, the checking in step S7 has a positive result, procedure is stopped in a step S8, which in case of a granulation process means that the mixing is stopped and that the contents may be dispensed from the granulation vessel for further processing in another processing structure.

It should be noted that FIGS. 2a and 2b merely gives an illustrative example of how to implement the method in the processing of pharmaceutical materials. Measurement and analysis corresponding to step S4 may e.g. be made also between steps S2 and S3, or simultaneously with S3.

As has been previously explained the prior art methods for monitoring and controlling the process in a processing vessel have been rather imprecise. The present invention allows for analysis of the parameter contents which provide information that has not been obtainable by the prior art methods. For instance, according to at least one embodiment of the invention a method is provided for determining the combination of parameter values of the contents, using the previously mentioned equation:

$$\varepsilon^a(f, T, LC) = \varepsilon_L^a(f, T) \cdot V_L + \varepsilon_{Air}^a V_{Air} + \sum_{i=1}^{N} \varepsilon_{M_i}^a(f, T, LC) \cdot V_{M_i}$$

wherein all the parameters can be well estimated. This may be compared with existing methods with which several of the parameters are difficult or even impossible to estimate adequately. The above equation will be used as a basis for the discussion of the FIGS. 3a and 3b, however, the invention as defined by the independent claim also encompasses other alternatives. Since there is no existing method which can provide an estimate of all the parameters, the parameter values obtainable by the present invention will, for the sake of exemplification, be compared with a simulated spectral measurements.

Figure 3A:
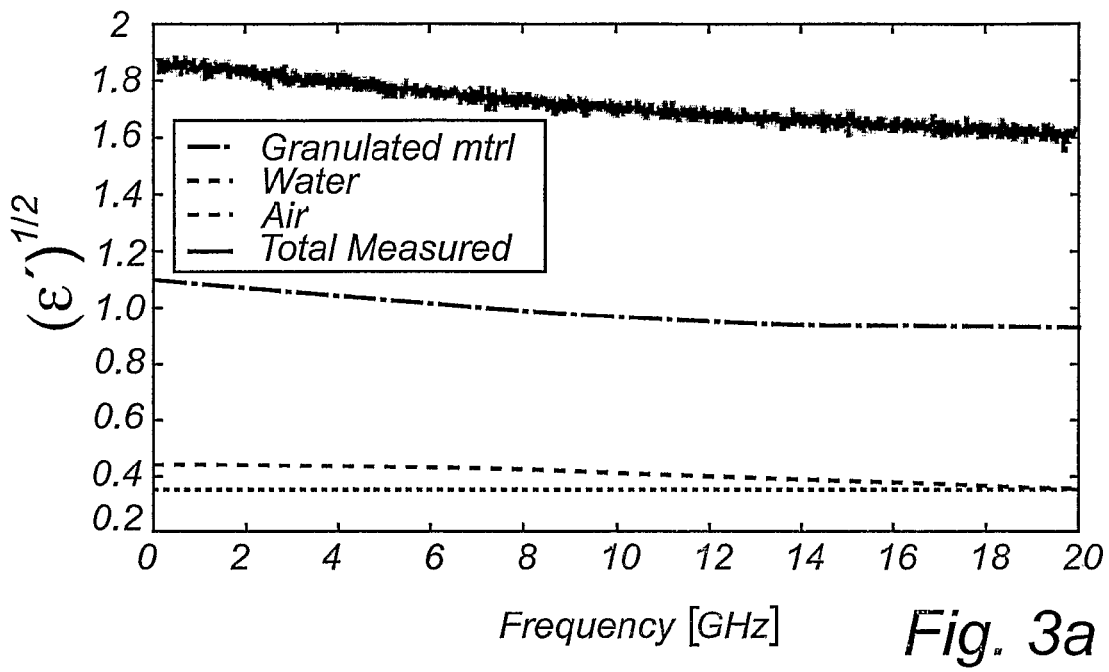
FIGS. 3a and 3b illustrate schematically graphs of the spectral contents in a processing vessel and also the assumed contributions from different substances of the contents.
Figure 3B:
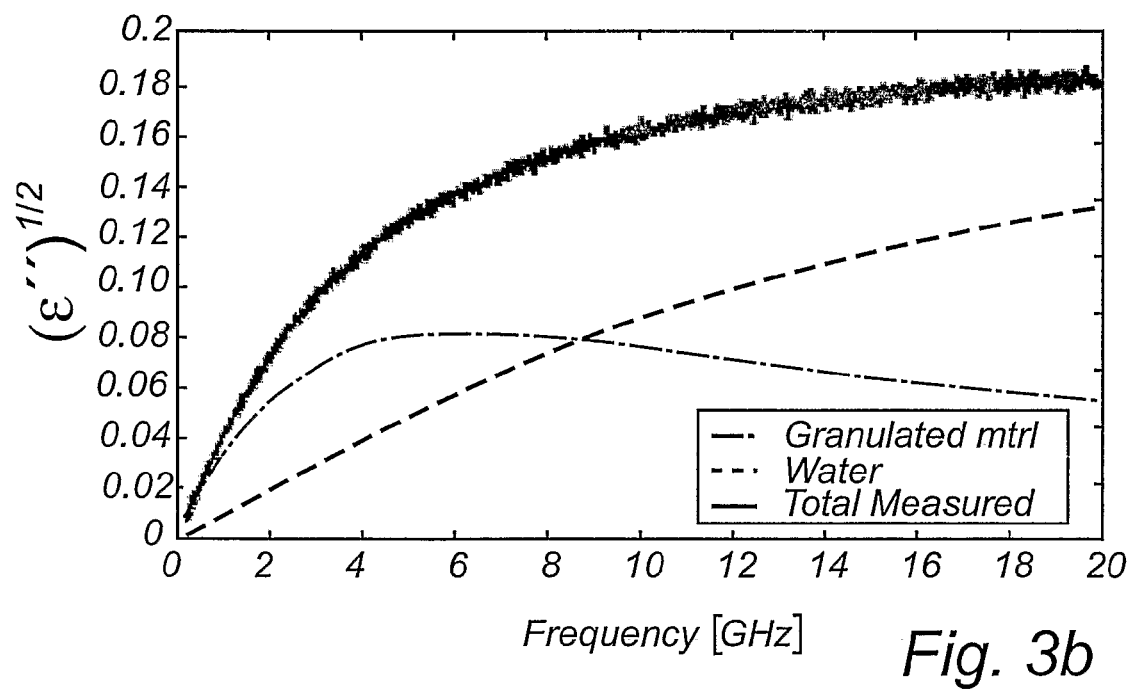

Thus, FIGS. 3a and 3b illustrate schematically exemplary graphs of a simulated spectral measurement of contents in a granulation vessel and also the assumed simulated contributions from different substances of the contents. In the example it is assumed that the dielectric constant $\in = \in' - j\in''$ of the granulated material is measured as a function of frequency in the interval 0.2 to 20 GHz. In order to perform a process control the measurement is performed in-line. The measurement could be performed using a reflection or a transmission mode. An advantage of the latter is that the information is obtained from a certain volume of the material, in contrast to the former wherein the information from the surface would be dominant. In this example pure water is used as the binding material. The presented approach should be applicable to any material combinations. Assuming that the dielectric properties of the granulated material $\in_M$ are modelled as a function of the frequency f, the water content WC of the material and its temperature T and using the fact that the f and the T dependence of the dielectric properties of pure water $\in_{Water}$ are well described by the Debye equation (using the results of the model constants presented in Fawwaz, T. U., R. K. Moore, and A. K. Fung, 1986. Microwave Remote Sensing: Active and Passive, Vol. III: From Theory to Applications, pp. 2020-2022, ISBN 0-89006192-0) the following model, which is a special case of the previously mentioned equation, may be built for the total dielectric constant $\in(f,T,WC)$:

$$\in^a(f,T,WC) = \in_M^a(f,T,WC) \times V_M + \in_{Water}^a(f,T) \times V_{Water} + V_{Air}$$

where $i \in$ (M, Water, Air), $V_i$ is the volumetric ratio of substance i to the total volume V, and in the last term the approximation $\in_{Air} \cong 1-j0$ was used. Suggested values in the literature for the power constant a are $$a \in \left(\frac{1}{2}, \frac{1}{3}\right),$$

where the value of ½ was selected. In this exemplary simulated granulation system the second term in the above equation will account for any water not absorbed by the granulated material (having a behaviour reminding more that of a bulk water). The last term takes into account the changing total density of the measured granulation mass.

The simulation was performed in the following way:

1. A certain process state was assumed: in this example T=27° C., granulated material water content of 15%, and volumetric distributions shown below in Table 1. Using these values and the model values for $\in_M$ and $\in_{Water}$ for these conditions and frequencies a spectrum was generated of the total complex dielectric constant $\in$, FIG. 3a illustrating the real part and FIG. 3b illustrating the imaginary part. Once generated those spectra were disturbed by additive Gaussian noise with different magnitudes (see Table 1) in order to simulate real observations taken for example in-line. FIGS. 3a and 3b display the assumed spectral contributions from the separate components as well as the simulated noisy in-line measured spectrum (the thick line in the figures). It should also be noted that the sum of the dielectric contributions of granulated material, water and air illustrated by the curves in FIGS. 3a and 3b equals the total measured dielectric constant.

2. Next it was assumed that the thus simulated spectrum is the in-line measurement. It was then attempted to retrieve, based on that spectrum, the water content absorbed in the granulated material, the temperature of the system and the volumetric ratios of the above mentioned components. Table 1 presents the values of the simulated and the retrieved after inverting the above equation estimates. To retrieve the unknowns a non-linear least squares inversion procedure was used. Case 1 refers to a case where the temperature T is regarded as unknown, while in Case 2 and Case 3 it is assumed that the temperature is measured using some external method. The advantage of Cases 2 and Case 3 is that due to the less unknowns to be estimated it can tolerate an order of magnitude larger measurement error while the former case will require a more noiseless measurements. However, the former has the advantage of avoiding the need for an additional sensor. Note that in Case 1 and Case 2 the same measurement error magnitude was used, wherein Case 2 provided the best result. In the simulations of Case 2 and Case 3, which both had separate temperature measurements, different measurement error magnitudes were used, resulting in a better estimation for Case 2 due to the lower measurement error.

Parameter values used in the simulation and their estimates after the inversion of Eq. 1. Results from three different cases are presented: 1) assuming that the temperature is one of the unknowns, 2) assuming the temperature as known and the same measurement error as in the first case, and 3) assuming the temperature as known and a different measurement error.

TABLE 1

|  | Water content in granulated material [%] | Granulated material vol. ratio [%] | Bulk water vol. ratio [%] | Air vol. ratio [%] | Temp. [T°] | Assumed meas. error [%] |
|---|---|---|---|---|---|---|
| Simulated | 15.0 | 60 | 5 | 35 | 27.0 | — |
| Estimated case 1 | 14.4 | 61 | 5 | 33 | 29.4 | 0.5 |
| Estimated case 2 | 14.8 | 61 | 5 | 35 | — | 0.5 |
| Estimated case 3 | 14.6 | 56 | 5 | 40 | — | 3 |

The information acquired in this way about the water content in the granulation material as well as the other estimated parameters may provide an indication on how the granulation process is evolving. For example a measurement of the process during wetting of the granulation material may indicate if there is a need for an active control, which may be applied by for example changing the water addition rate or the impeller speed. The in-line information acquired in this way could also be used after the completion of the granulation process to check if the process has been conducted in the expected way and if not make note for future quality check of the final product arising from this particular granulation.

It should be noted that the information obtained by means of the equation above may also be used for estimating the values of other parameters. For instance, the density of the contents may be estimated from the volumetric ratio $V_i$, since the densities of the wet granulated material and the water could be known. Also the water state may be estimated, i.e. how much of the water is free and how much is bound to the granulated material. Any water that has been trapped among granulated material particles but has not been absorbed (bound) will substantially be measured as free water together with the rest of the free water and will be detected as $V_{Water}$. Thus, if the starting values are known and the amount of water added is known, the water state may be estimated by means of the equation above. This may be an interesting parameter to estimate, since it affects the formation of the granules. Thus, while the amount of water present in the contents provides some information, the amount of water that has been bound or absorbed by the material may provide other information relevant to the monitoring of the progress of the process.

Figure 4:
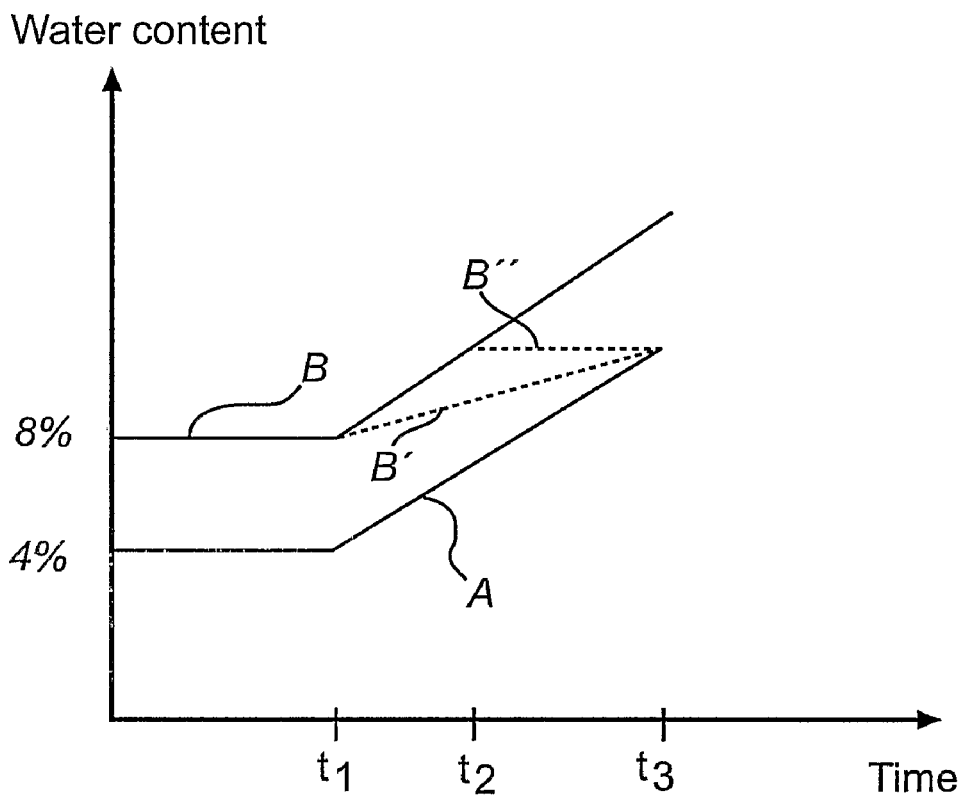
FIG. 4 illustrates schematically a graph of different starting values of water content in a material as a function of time.

FIG. 4 illustrates schematically a graph of different starting values of water content in a material as a function of time. The graph will be explained as relating to a granulation process, however, it may be applicable to other pharmaceutical processes as well. In the graph of FIG. 4 two curves A and B are shown. Curve A represents a situation in which the material has a water content of 4% before the start of the granulation process. Curve B represents a situation in which the material has a water content of 8% before the start of the granulation process. After the granulation process has started, the material is dry-mixed during a period of time $t_1$. During this period no extra water is added to the material, and thus the water content remains unchanged, which is illustrated by the horizontal extensions of curves A and B. At time $t_1$ water is added so as to promote the formation of granules. If the water is added at the same rate in both situations A and B, the water content will be larger in situation B than in situation A at time $t_3$ when the adding of water has been completed.

Figure 5:
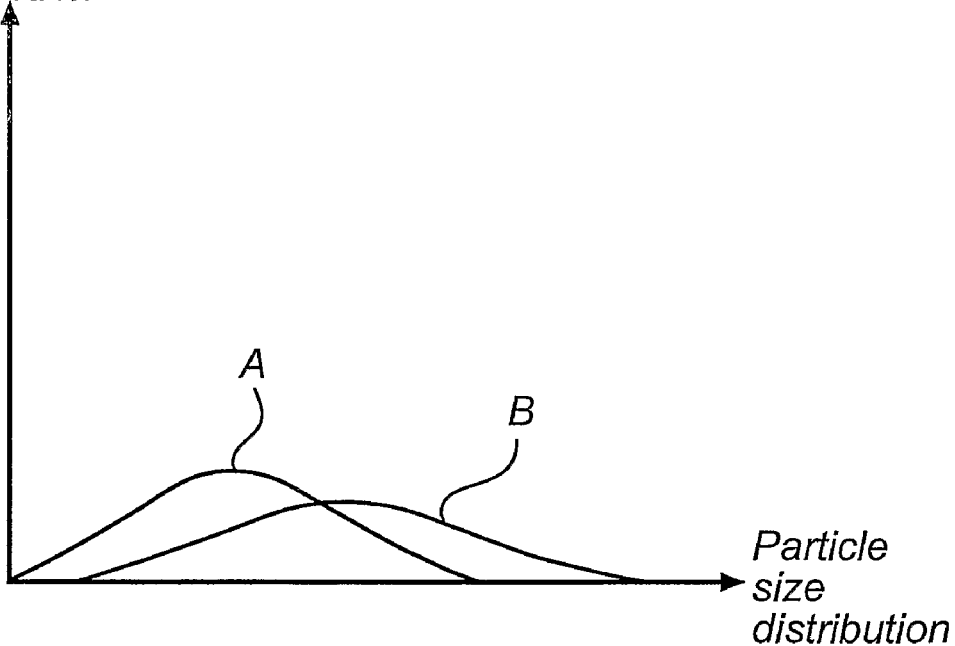
FIG. 5 illustrates schematically, for the material having said different starting values of water content in FIG. 4, a graph of probability density as a function of particle size distribution at a certain point of time.

The difference in the water content of the granulated material may result in different particle size distribution. FIG. 5 illustrates schematically a graph of probability density as a function of particle size distribution at said time $t_3$. Thus, the particle size distribution for situation B, in which the water content starting value was 8%, is different from the particle size distribution for situation A, in which the water content starting value was 4%. If, for instance, it has been found that the particle size distribution according to situation A provides better tabletting properties than the particle size distribution according to situation B, then it would be desirable to control the granulation process so as to obtain the appropriate particle size distribution even if the starting material has a water content which is different from 4%. Thus, if a measurement has been made in accordance with the inventive method at the beginning of a granulation process, and the measurement has shown that the water content is 8% as illustrated by curve B in FIG. 4, the adding of water may be suitably controlled. One alternative is to add the water at a slower rate after the dry-mixing period, i.e. at time $t_1$ so that the water content at time $t_3$ will be the desired one. This is illustrated by the dashed line B'. Another alternative is to, at time $t_1$, add the water at a normal rate, and continue performing measurements. When the desired water content has been reached at time $t_2$, no more water is added for the rest of the wet-mixing period between times $t_2$ and $t_3$. This is illustrated by dashed line B". Yet another alternative would be to add water at a time between times $t_2$ and $t_3$, or to add in several steps rather than at a continuous rate. Suitably, measurements are performed at several instances and the result is fed to a control loop.

It should be noted that the amounts of 4% and 8% are merely given herein as elucidating examples, and it should be understood that the underlying idea of controlling the process is applicable to other percentages as well. Similarly, the control of the water content and/or particle size distribution are only elucidating examples of controllable parameters, and it should be understood that other parameters may also be controlled. For instance, the speed of the mixing arrangement, such as an impeller, may also be controlled for obtaining the desired particle size distribution. It may either be controlled alone, or in combination with the control of water addition. Another alternative would be to control the torque angle of the impeller.

The invention claimed is:

1. A method of analyzing contents in a pharmaceutical processing vessel, wherein the contents include at least a pharmaceutical material and have a plurality of predefined parameters of variable values, the method comprising:
transmitting electromagnetic radiation at various frequencies into the contents in the vessel;
receiving electromagnetic radiation that has interacted with the contents;
determining a respective value of a physical quantity related to the contents for each of a plurality of the frequencies, by comparing the received electromagnetic radiation with the transmitted electromagnetic radiation; and
determining a combination of values of said predefined parameters that would, for each of the plurality of frequencies, approximately result in the determined values of said physical quantity, by modeling the physical quantity as a function of a volumetric ratio of a volume of the pharmaceutical material in the contents to a total volume of the contents.

2. The method of claim 1, wherein said physical quantity of the contents reflects a dielectric constant, wherein the method comprises:
determining, for a plurality of said frequencies, the respective dielectric constant of the contents based on the received electromagnetic radiation; and
determining a combination of values of said predefined parameters that would, for said plurality of frequencies, approximately result in the determined dielectric constants.

3. The method of claim 2, wherein said step of determining a combination of values of said predefined parameters comprises solving the following equation for each dielectric constant $\in(f, T, LC)$, determined for a respective frequency:

$$\varepsilon^a(f, T, LC) = \varepsilon_L^a(f, T) \cdot V_L + \varepsilon_{Air}^a V_{Air} + \sum_{i=1}^{N} \varepsilon_{M_i}^a(f, T, LC) \cdot V_{M_i}$$

wherein, for a number of N different pharmaceutical materials:
$V_{M_i}$ is the volumetric ratio of the i:th pharmaceutical material to the total contents volume V,
$\in_{M_i}$ is the dielectric constant of the i:th pharmaceutical material,
$V_L$ is the volumetric ratio of a liquid, such as water, to the total contents volume V,
$\in_L$ is the dielectric constant of a liquid,
$V_{Air}$ is the volumetric ratio of air to the total contents volume V,
$\in_{Air}$ is the dielectric constant of air,
f is the frequency,
T is the temperature of the contents in the vessel,
LC is the liquid content of the material, and
a is a power law constant.

4. The method of claim 1, wherein said physical quantity of the contents reflects a phase and/or an amplitude of the received electromagnetic radiation, wherein the method comprises:
determining, for a plurality of said frequencies, a respective phase and/or amplitude change between the received and transmitted electromagnetic radiation; and
determining a combination of values of said predefined parameters that would, for said plurality of frequencies, approximately result in the determined phase and/or amplitude changes.

5. The method of claim 1, wherein said step of determining a combination of values of said predefined parameters further includes determining the combination of values by at least one of:
an empirical broad parameter space calibration;
a theoretical physical modeling of the interaction of the electromagnetic radiation with the contents in the vessel; and
a multivariate analytical method selected from one of Principal Component Analysis (PCA) and Projections to Latent Structures (PLS).

6. The method of claim 1, wherein said plurality of frequencies are in the range of 100 MHz-10 THz.

7. The method of claim 1, wherein at least said steps of transmitting electromagnetic radiation, receiving electromagnetic radiation, and determining said values of a physical quantity are performed continuously or repeatedly for obtaining data related to processing the contents.

8. The method of claim 1, wherein the predefined parameters of the contents are any combinations selected from the group consisting of: a temperature of the contents; a density of the contents; a water state/bounding value of the contents; a water content value; and a volumetric ratio of one or more substances in the contents, such substances suitably being pharmaceutical material, water, and/or air.

9. A method of treating contents in a pharmaceutical processing vessel, wherein the contents include at least a pharmaceutical material and have a plurality of predefined parameters of variable values, the method comprising:
transmitting electromagnetic radiation at various frequencies into the contents in the vessel;
receiving electromagnetic radiation that has interacted with the contents;
determining a respective value of a physical quantity related to the contents for each of a plurality of the frequencies, by comparing the received electromagnetic radiation with the transmitted electromagnetic radiation;
determining a combination of values of said predefined parameters that would, for each of the plurality of frequencies, approximately result in the determined values of said physical quantity, by modeling the physical quantity as a function of a volumetric ratio of a volume of the pharmaceutical material in the contents to a total volume of the contents; and controlling a process for treating the contents based on at least one parameter value from the determined combination of values.

10. The method as claimed in claim 9, comprising:

determining deviations of said at least one parameter value from a reference value for said parameter;

extracting information related to a state of the process based on the determined deviations; and controlling the process based on the extracted information.

11. The method of claim 9, wherein said process is a high-shear granulation process for processing the contents in a high-shear granulation vessel.

12. The method of claim 9, wherein the step of controlling the process comprises controlling a process parameter, the process parameter being at least one selected from the group consisting of:

an amount, speed, or rate of water or other liquid introduced into the processing vessel; a point of time when water or other liquid is to be introduced into the processing vessel; a point of time for ending the process; a location for introducing water or other liquid, or a direction of nozzles for said introduction; an output or rotational speed of a mixing device; and a torque angle of the mixing device.

13. The method of claim 9, wherein said process is a drying process for drying the contents in a drying vessel.

14. The method of claim 9, wherein said process is a blending process for blending the contents in a mixing apparatus.

15. The method of claim 9, wherein the combination of values is determined at least before starting the process for treating the contents in the pharmaceutical processing vessel.

16. The method of claim 9, wherein the step of determining a combination of values of said predefined parameter is performed after the process for treating the pharmaceutical contents in the pharmaceutical processing vessel is completed.

17. The method of claim 9, wherein said parameters of the contents are any combinations selected from the group consisting of: a temperature of the contents; a density of the contents; a water state/bounding value of the contents; a water content value; and a volumetric ratio of one or more substances in the contents, such substances suitably being pharmaceutical material, water, and/or air.

18. The method of claim 9, wherein said step of determining a combination of values of said predefined parameters further includes determining the combination of values by at least one of:

an empirical broad parameter space calibration;

a theoretical physical modeling of the interaction of the radiation energy with the contents in the vessel, and a multivariate analytical method selected from one of Principal Component Analysis (PCA) and Projections to Latent Structures (PLS).

19. The method of claim 9, wherein said physical quantity of the contents is a dielectric constant, and said step of determining a combination of values of said predefined parameters comprises solving the following equation for each dielectric constant $\in(f, T, LC)$, determined for a respective frequency:

$$\varepsilon^\alpha(f, T, LC) = \varepsilon_L^\alpha(f, T) \cdot V_L + \varepsilon_{Air}^\alpha V_{Air} + \sum_{i=1}^{N} \varepsilon_{M_i}^\alpha(f, T, LC) \cdot V_{M_i}$$

wherein, for a number of N different pharmaceutical materials:

$V_{M_i}$ is the volumetric ratio of the i:th pharmaceutical material to the total contents volume V, $\in_{M_i}$ is the dielectric constant of the i:th pharmaceutical material, $V_L$ is the volumetric ratio of a liquid to the total contents volume V, $\in_L$ is the dielectric constant of a liquid, $V_{Air}$ is the volumetric ratio of air to the total contents volume V, $\in_{Air}$ is the dielectric constant of air, which may preferably be approximated to 1-j0, f is the frequency, T is the temperature of the contents in the vessel, LC is the liquid content of the material, and a is a power law constant.

20. A method of treating contents in a pharmaceutical processing vessel, wherein the contents include a pharmaceutical material and have a plurality of predefined parameters of variable values, the method comprising:

transmitting electromagnetic radiation at frequencies ranging between 300 MHz and 300 GHz into the contents in the vessel;

receiving electromagnetic radiation that has interacted with the contents;

determining a value of a physical quantity related to the contents for each of a plurality of the frequencies, by comparing the received electromagnetic radiation with the transmitted electromagnetic radiation;

determining a combination of values of said predefined parameters that would, for each of the plurality of frequencies, approximately result in the determined values of said physical quantity, by modeling the physical quantity as a function of a volumetric ratio of a volume of the pharmaceutical material in the contents to a total volume of the contents; and controlling a process for treating the contents based on at least one parameter value from the determined combination of values, by adding one or more of water and the pharmaceutical material.

* * * * *

UNITED STATES PATENT AND TRADEMARK OFFICE
CERTIFICATE OF CORRECTION

| | | |
|---|---|---|
| PATENT NO. | : 7,825,668 B2 | Page 1 of 1 |
| APPLICATION NO. | : 11/793391 | |
| DATED | : November 2, 2010 | |
| INVENTOR(S) | : Staffan Folestad and Lubomir Gradinarsky | |

It is certified that error appears in the above-identified patent and that said Letters Patent is hereby corrected as shown below:

Claim 3, col. 18, line 7, delete ",such as water,".

Claim 16, col. 19, line 40, "predefined parameter" should read -- predefined parameters --.

Signed and Sealed this
Fifteenth Day of March, 2011

David J. Kappos
*Director of the United States Patent and Trademark Office*